US012698251B2

(12) United States Patent
Brammer et al.

(10) Patent No.: US 12,698,251 B2
(45) Date of Patent: Aug. 4, 2026

(54) PROCESSES TO IMPROVE CATALYTIC METAL ACCOUNTABILITY IN HYDROFORMYLATION PROCESSES

(71) Applicant: Dow Technology Investments LLC, Midland, MI (US)

(72) Inventors: Michael A. Brammer, Lake Jackson, TX (US); Jason F. Giles, Missouri City, TX (US); Glenn A. Miller, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 500 days.

(21) Appl. No.: 18/251,009

(22) PCT Filed: Nov. 18, 2021

(86) PCT No.: PCT/US2021/059810

§ 371 (c)(1),
(2) Date: Apr. 28, 2023

(87) PCT Pub. No.: WO2022/132372

PCT Pub. Date: Jun. 23, 2022

(65) Prior Publication Data

US 2023/0406801 A1 Dec. 21, 2023

Related U.S. Application Data

(60) Provisional application No. 63/124,922, filed on Dec. 14, 2020.

(51) Int. Cl.
*C07C 45/50* (2006.01)
*B01J 31/18* (2006.01)

(52) U.S. Cl.
CPC ........... *C07C 45/505* (2013.01); *B01J 31/185* (2013.01)

(58) Field of Classification Search
CPC ... C07C 45/505; B01J 31/185; B01J 31/4092; B01J 2531/822
See application file for complete search history.

(56) References Cited

U.S. PATENT DOCUMENTS

| | | | |
|---|---|---|---|
| 414,883 | A | 11/1889 | Harrison et al. |
| 4,277,627 | A | 7/1981 | Bryant et al. |
| 4,717,775 | A | 1/1988 | Billig et al. |
| 4,769,498 | A | 9/1988 | Billig et al. |
| 4,774,361 | A | 9/1988 | Maher et al. |
| 4,792,636 | A | 12/1988 | Hensman et al. |
| 5,741,944 | A | 4/1998 | Bryant et al. |
| 6,090,987 | A | 7/2000 | Billig et al. |
| 6,500,991 | B2 | 12/2002 | Wiese et al. |
| 8,404,903 | B2 | 3/2013 | Cox et al. |
| 10,023,516 | B2 | 7/2018 | Brammer et al. |
| 2017/0253549 | A1 | 9/2017 | Miller et al. |
| 2017/0355656 | A1 | 12/2017 | Brammer et al. |

FOREIGN PATENT DOCUMENTS

| | | |
|---|---|---|
| EP | 3222344 | 9/2017 |
| KR | 1060375 | 8/2011 |
| WO | 2016089602 | 6/2016 |
| WO | 2019/112866 | 6/2019 |
| WO | 2020/112373 | 6/2020 |

OTHER PUBLICATIONS

PCT/US2021/059810 International Search Report and Written Opinion with a mailing date of Mar. 3, 2022.

*Primary Examiner* — Sikarl A Witherspoon

(57) ABSTRACT

Embodiments of the present invention are directed to processes to improve rhodium accountability in continuous liquid recycle hydroformylation processes. In some embodiments, a process comprises contacting in a reaction zone reactants comprising C7-C20 olefins, hydrogen, and carbon monoxide in the presence of a catalyst comprising rhodium and an organomonophosphite ligand to form a reaction fluid, wherein the feed rate of olefins to the reaction zone is greater than 100 kilograms/hour; providing the reaction fluid to a strip gas vaporizer to produce a product stream and a vaporizer tails stream; measuring the C7-C20 olefin content in the vaporizer tails stream; and adding a C7-C20 olefins stream comprising at least 50 weight percent C7-C20 olefins to the vaporizer tails stream to maintain the C7-C20 content in vaporizer tails stream above 2 percent by weight.

7 Claims, No Drawings

PROCESSES TO IMPROVE CATALYTIC METAL ACCOUNTABILITY IN HYDROFORMYLATION PROCESSES

FIELD

The present invention relates to processes to improve rhodium accountability in continuous liquid recycle hydroformylation processes.

BACKGROUND

It is well known that aldehydes can be produced by reacting olefins with carbon monoxide and hydrogen in the presence of a metal-organophosphorus ligand complex catalyst. Such processes can involve continuous hydroformylation and recycling of a catalyst solution containing a metal-organophosphorus ligand complex catalyst wherein the metal is selected from Groups 8, 9, or 10. Rhodium is a common Group 9 metal used in the metal-organophosphorus ligand complex catalyst for hydroformylation. Examples of such processes are disclosed in U.S. Pat. Nos. 4,148,830, 4,717,775, and 4,769,498. The resulting aldehydes can be used to produce a host of products including alcohols, amines, and acids.

Hydroformylation catalysts comprising rhodium and bulky organomonophosphite ligands are capable of very high reaction rates. See, e.g., "Rhodium Catalyzed Hydroformylation," van Leeuwen, Claver, Kluwer Academic Pub. (2000). Such catalysts have industrial utility as they can be used to increase production rates, or to efficiently hydroformylate internal and/or branched internal olefins which react more slowly than linear alpha olefins.

Under some conditions, rhodium-bulky organomonophosphite catalysts have been known to suffer an irretrievable loss of rhodium in liquid recycle hydroformylation processes. See, e.g., U.S. Pat. No. 4,774,361. Although the exact cause of rhodium loss is unclear, it has been hypothesized that the rhodium loss is exacerbated by the product separation step, which is commonly achieved through vaporization and condensation of the product overhead, leaving a residual stream that includes higher boiling by-products and the non-volatile catalyst (vaporizer tails) which is then recycled back to the reaction zone. Vaporization of the products derived from higher olefins (e.g., C7 or higher) requires higher temperatures which are also known to exacerbate rhodium loss. A continuous loss of rhodium can increase catalyst costs dramatically, as rhodium is prohibitively expensive.

There remains a need for continuous liquid recycle hydroformylation processes that improve rhodium accountability, particularly when hydroformylating C7 or higher olefins using highly active rhodium-organomonophosphite catalysts.

SUMMARY

The present invention relates to processes for hydroformylating C7 and higher (e.g., C7-C20) olefins using continuous liquid recycle that improve rhodium accountability. It has been surprisingly found that by maintaining a concentration of at least 2 percent by weight of C7 and higher olefins in a vaporizer tails stream from a strip gas vaporizer, the rhodium accountability will improve. That is, the amount of rhodium loss in the process will be reduced. This can be accomplished, for example, by feeding a portion of the olefin feed directly after the product/catalyst separation zone (the strip gas vaporizer) such as to the vaporizer catch pot or just after the vaporizer catch pot pump such that the vaporizer tails from that point to the reaction zone contain at least 2 percent by weight of C7 and higher olefins.

In one aspect, a process to improve rhodium accountability in a continuous liquid recycle hydroformylation process comprises contacting in a reaction zone reactants comprising C7-C20 olefins, hydrogen, and carbon monoxide in the presence of a catalyst comprising rhodium and an organomonophosphite ligand to form a reaction fluid, wherein the feed rate of olefins to the reaction zone is greater than 100 kilograms/hour; providing the reaction fluid to a strip gas vaporizer to produce a product stream and a vaporizer tails stream; measuring the C7-C20 olefin content in the vaporizer tails stream; and adding a C7-C20 olefins stream comprising at least 50 weight percent C7-C20 olefins to the vaporizer tails stream to maintain the C7-C20 content in vaporizer tails stream above 2 percent by weight.

In one aspect, a process to improve rhodium accountability in a continuous liquid recycle hydroformylation process comprises contacting in a reaction zone reactants comprising mixed C8 olefins, hydrogen, and carbon monoxide in the presence of a catalyst comprising rhodium and an organomonophosphite ligand to form a reaction fluid, wherein the feed rate of olefins to the reaction zone is greater than 100 kilograms/hour; providing the reaction fluid to a strip gas vaporizer to produce a product stream and a vaporizer tails stream; measuring the C8 olefin content in the vaporizer tails stream; and adding a C8 olefins stream comprising at least 50 weight percent C8 olefins to the vaporizer tails stream to maintain the C8 content in vaporizer tails stream above 2 percent by weight.

In one aspect, a process to improve rhodium accountability in a continuous liquid recycle hydroformylation process comprises contacting in a reaction zone reactants comprising mixed C9 olefins, hydrogen, and carbon monoxide in the presence of a catalyst comprising rhodium and an organomonophosphite ligand to form a reaction fluid, wherein the feed rate of olefins to the reaction zone is greater than 100 kilograms/hour; providing the reaction fluid to a strip gas vaporizer to produce a product stream and a vaporizer tails stream; measuring the C9 olefin content in the vaporizer tails stream; and adding a C9 olefins stream comprising at least 50 weight percent C9 olefins to the vaporizer tails stream to maintain the C9 content in vaporizer tails stream above 2 percent by weight.

These and other embodiments are discussed in more detail in the Detailed Description below.

DETAILED DESCRIPTION

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference).

As used herein, "a," "an," "the," "at least one," and "one or more" are used interchangeably. The terms "comprises," "includes," and variations thereof do not have a limiting meaning where these terms appear in the description and claims.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

As used herein, the term "ppmw" means parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "catalyst fluid", "process fluid", "reaction fluid," "reaction medium" and "catalyst solution" are used interchangeably herein, and may include, but are not limited to, a mixture comprising: (a) a metal-organomonophosphite ligand complex catalyst, (b) free organomonophosphite ligand, (c) aldehyde product formed in the reaction, (d) unreacted reactants, (e) a solvent for said metal-organomonophosphite ligand complex catalyst and said free organomonophosphite ligand, and, optionally, (f) one or more compounds resulting from degradation of the organomonophosphite ligand; such ligand degradation products may be dissolved and/or suspended. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated to remove ligand degradation products or other impurities, (g) a treated or untreated fluid returned to a reaction zone or separation zone, (h) a fluid in an external cooler, and (i) ligand decomposition products and components derived from them, such as oxides, sulfides, salts, oligomers, and the like. "Organomonophosphite ligands" are trivalent phosphorous ligands that contain three P—O bonds.

The term "free ligand" means ligand that is not coordinated to a transition metal.

For the purposes of this invention, the terms "heavy byproducts" and "heavies" are used interchangeably and refer to liquid byproducts that have a normal boiling point that is at least 25° C. above the normal boiling point of the desired product of the hydroformylation process. Such materials are known to form inherently in hydroformylation processes under normal operation through one or more side reactions, including for example, by aldol condensation.

For the purpose of this invention, the term "dimer" in reference to heavies refers to heavy byproducts derived from two molecules of aldehyde. Likewise the term "trimer" refers to heavy byproducts derived from three molecules of aldehyde (e.g. C9 aldehyde trimer).

For the purposes of this invention, the terms "reaction zone" and "reactor" are used interchangeably and refer to a region of the process containing reaction fluid and wherein both olefins and syngas (synthesis gas) are added at elevated temperatures.

For the purposes of this invention, the terms "separation zone" and "vaporizer" are used interchangeably and refer to a region where the reaction fluid is heated (i.e. the temperature is higher than the reaction zone temperature) causing an increase in the vapor pressure of the product aldehyde. The resulting gaseous phase is then passed through a condenser to allow collection of the product as a liquid; the non-volatile concentrated effluent (tails, or vaporizer tails) containing the homogeneous catalyst is then returned to one or more of the reactors. The separation zone may optionally be operated at reduced pressure.

For the purposes of this invention, the term "strip gas vaporizer" refers to a vaporizer featuring a flowing gas that aids in product removal. Details of an exemplary strip gas vaporizer may be found in U.S. Pat. No. 8,404,903.

For the purposes of this invention, the term "CO strip gas vaporizer" refers to an embodiment of a strip gas vaporizer wherein the partial pressure of carbon monoxide in the strip gas is ≥16 psi [≥0.110 MPa]. Details of an exemplary CO strip gas vaporizer may be found in U.S. Pat. No. 10,023,516.

For the purposes of this invention, the term "strip gas" refers to the flowing gas employed in a strip gas vaporizer. The strip gas is comprised of CO, and optionally hydrogen, and inert gases (e.g., methane, argon, and nitrogen), and may be added directly to the vaporizer on a continuous basis, as well as small amounts of CO, hydrogen, aldehydes, olefins and alkanes which move from the reaction fluid into the vapor phase during operation. The aldehyde-laden gaseous effluent from the strip gas vaporizer is passed through a condenser ("strip gas condenser") to generate a crude liquid product stream, and a stream of uncondensed gases. At least a portion of the uncondensed gases are then recycled to the vaporizer ("recycle gas") using a compressor or blower. Strip gas thus refers to the gaseous stream flowing through the strip gas vaporizer comprising both fresh gases which are continually introduced to the process, and recycle gas.

For the purposes of this invention, the terms "feed to tails" and "feed to tails ratio" are used interchangeably and refer to the mass of reaction fluid entering the separation zone (e.g., strip gas vaporizer) relative to the mass of vaporizer tails leaving the bottom of the separation zone (e.g., strip gas vaporizer) and returning to the hydroformylation reactors. "Feed to tails" is an indicator of the rate at which volatiles, such as aldehyde product, are removed from the reaction fluid. For example, a "feed to tails ratio" of 2, means that the weight of reaction fluid entering the separation zone (e.g., strip gas vaporizer) is two times greater than the weight of the concentrated effluent returned to the hydroformylation reactors.

For the purposes of this invention, the terms "liquid-recycle", "liquid-recycle hydroformylation", and "liquid-recycle process" are used interchangeably and are contemplated to comprise a hydroformylation process wherein the process fluid is introduced to a separation zone to produce a tails stream comprising the catalyst which is returned to the reaction zone. Examples of such processes are given in U.S. Pat. Nos. 4,148,830 and 4,186,773.

For the purposes of this invention, the term "C7-C20 olefins" refers to an isolated (non-conjugated) unsaturated hydrocarbon (mono-olefin) of 7 to 20 carbons which may be terminal or internal with or without branches. The material may be a single isomer or a mixture of isomers and may include a mixture of olefins, the majority of which are C7 and higher (up to C20). It is to be understood that the feed may also contain saturated hydrocarbon impurities. The unsaturation is not part of an aromatic ring such as toluene. The preferred olefins are those with higher levels of terminal olefins, preferably with no branches next to the olefin. In some embodiments, the olefins have less than 15 carbons ("C7-C15 olefins") and in some embodiments, less than 12 carbons ("C7-C12 olefins").

For the purposes of this invention, the terms "mixed C8 olefins" and "mixed octenes" are used interchangeably and refer to the primary olefin feed comprised of singly unsaturated compounds containing eight carbon atoms and hydrogen. This includes 1-octene, C8 internal olefins and branched terminal olefins such as 2-methyl-1-heptene, 3-methyl-1-heptene, 2-ethyl-1-hexene and the like.

For the purposes of this invention, the term "C8 internal olefins" refers to all isomers of singly unsaturated compounds comprised of eight carbon atoms wherein the double bond is not in the terminal position. Examples of C8 internal olefins include, cis-2-octene, trans-2-octene, cis-3-octene, trans-3-octene, cis-4-octene, trans-4-octene, 3-methyl-2-heptene, 3-methyl-3-heptene, 5-methyl-2-heptene, 5-methyl-3-heptene, 3,4-dimethyl-2-hexene, 3,4-dimethyl-3-hexene, 2,3-dimethyl-3-hexene and the like.

For the purposes of this invention, the terms "mixed C9 olefins" and "mixed nonenes" are used interchangeably and refer to the primary olefin feed comprised of singly unsaturated compounds containing nine carbon atoms and hydrogen. This includes 1-nonene, C9 internal olefins and branched terminal olefins such as 2,3-dimethyl-1-heptene, 4,6-dimethyl-1-heptene, 4,6-dimethyl-2-heptene, 4,6-dimethyl-3-heptene, 2,4-dimethyl-2-heptene, 2,6-dimethyl-1-heptene, 2,6-dimethyl-2-heptene, 2,4,5-trimethyl-1-hexene, 2,4,5-trimethyl-2-hexene, and the like.

For the purposes of this invention, the terms "C9 internal olefins" refers to all isomers of singly unsaturated compounds comprised of nine carbon atoms wherein the double bond is not in the terminal position. Examples of C9 internal olefins include, 2,4-dimethyl-2-heptene, 2,6-dimethyl-2-heptene, 2,4,5-trimethyl-2-hexene, 4,6-dimethyl-2-heptene, 4,6-dimethyl-3-heptene and the like.

For the purposes of this invention, the term "recycled olefin(s)" refers to mixed C7-C20 olefins (e.g., mixed C8 olefins in a C8 process or mixed C9 olefins in a C9 process) which have passed at least once through the hydroformylation reaction zone without being hydroformylated, and are then separated from the crude aldehyde product, for example, by distillation. The terms "recycled olefin(s)" and "recycled C8 olefin(s)" (and "recycled C9 olefin(s)" when discussing a C9 process) are used interchangeably herein. Preferably at least a portion of the olefin thus recovered is then returned to the reaction zone and most preferably a portion is used to stabilize the catalyst after the product/separation zone as described herein. Recycled olefin may also be returned to other parts of the process as desired and as described herein. Recycled C8 olefins are comprised largely of dimethyl hexenes which hydroformylate more slowly than linear octenes or methyl heptenes, thus single pass conversion may decline as the concentration of recycled olefin increases.

Hydrogen and carbon monoxide are required for the process. These may be obtained from any suitable source, including petroleum cracking and refinery operations. Syngas mixtures are preferred as a source of hydrogen and CO.

Syngas (from synthesis gas) is the name given to a gas mixture that contains varying amounts of CO and $H_2$. Production methods are well known and include, for example: (1) steam reforming and partial oxidation of natural gas or liquid hydrocarbons, and (2) the gasification of coal and/or biomass. Hydrogen and CO typically are the main components of syngas, but syngas may contain carbon dioxide and inert gases such as $CH_4$, $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

The olefin starting materials that may be employed in the hydroformylation process of this invention are C7-C20 olefins as defined herein. For example, in embodiments, when the olefin starting materials are mixed C8 olefins, the mixed C8 olefins include mixtures such as may be obtained via dimerization of mixed butenes comprising 1-butene, cis and trans-2-butene and optionally isobutene. In one embodiment, a stream comprising mixed octenes derived from the dimerization of Raffinate II is employed; such mixtures may be produced, for example by the Dimersol process from Axens (Institut Français du Petrole, Review, Vol. 37, No 5, September-October 1982, p 639) or the Octol process from Hüls AG (Hydrocarbon Processing, February 1992, p 45-46). It is understood that the olefin mixtures employed in the process of the invention may also comprise some amount of linear alpha olefins.

In some embodiments, the olefin starting materials are mixed C9 olefins as defined herein. Such mixtures may be available from a variety of sources and may be produced, for example by the process described in Johan A. Martens, Wim H. Verrelst, Georges M. Mathys, Stephen H. Brown, Pierre A. Jacobs "Tailored Catalytic Propene Trimerization over Acidic Zeolites with Tubular Pores", Angewandte Chemie International Edition Angewandte Chemie International Edition 2005, Volume 44, Issue 35, pages 5687-5690.

It should be understood that embodiments of the present invention are designed for use in processes where the olefin starting materials are C7-20 olefins such as described above. In some embodiments, the olefin starting materials are primarily mixed C8 olefins or mixed C9 olefins. However, it should be also understood that in processes designed for the hydroformylation of mixed C8 olefins, a small amount of mixed C9 olefins may also be present in the olefin starting materials. Likewise, it should be also understood that in processes designed for the hydroformylation of mixed C9 olefins, a small amount of mixed C8 olefins may also be present in the olefin starting materials.

A solvent advantageously is employed in the hydroformylation process. Any suitable solvent that does not unduly interfere with the hydroformylation process can be used. The organic solvent may also contain dissolved water up to the saturation limit. In rhodium catalyzed hydroformylation, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,830 and 4,247,486. Indeed, while one may employ, if desired, any suitable solvent at the start-up of a continuous process, the primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of two or more solvents may also be employed.

The catalyst useful in the hydroformylation process comprises a rhodium-organomonophosphite ligand complex. In general, such catalysts may be preformed or formed in situ and consist essentially of rhodium in complex combination with an organomonophosphite ligand, such as those disclosed for example in U.S. Pat. No. 4,567,306 and those discussed below, carbon monoxide and hydrogen.

In addition to the organomonophosphite ligand complexed to the metal, additional, or "free" ligand is employed. Mixtures of organomonophosphite ligands may be employed if desired. This invention is not intended to be limited in any manner by the permissible organomonophosphite ligands or mixtures thereof. It is to be noted that the successful practice of this invention does not depend and is not predicated on the exact structure of the metal-organomonophosphite ligand complex species, which may be present in their mononuclear, dinuclear and/or higher nuclearity forms. Indeed, the exact structure is not known. While not intending to be bound to any theory or mechanistic discourse, it appears that the catalytic species may in its simplest form consist essentially of the metal in complex combination with the organomonophosphite ligand and carbon monoxide and/or hydrogen.

The term "complex" as used herein means a coordination compound formed by the union of one or more electronically rich molecules or atoms capable of independent existence with one or more electronically poor molecules or atoms, each of which is also capable of independent existence. For example, the organomonophosphite ligands employable herein possess a phosphorus donor atom having one available or unshared pair of electrons capable of forming a coordinate bond with the metal. Carbon monoxide, which is also properly classified as a ligand, can also be present and coordinated to the metal. The ultimate composition of the complex catalyst may also contain an additional ligand, e.g., hydrogen or an anion satisfying the coordination sites or nuclear charge of the metal. Illustrative additional ligands include, for example, alkyl, aryl, substituted aryl, acyl, $CF_3$, $C_2F_5$, CN, $(R)_2PO$ and RP(O)(OH)O (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3$, $C_6HsCN$, $CH_3CN$, $NH_3$, pyridine, $(C_2H_5)_3N$, tetrahydrofuran, and the like. The complex species are preferably free of any additional organic ligand or anion that might poison the catalyst or have an undue adverse effect on catalyst performance. It is preferred in the rhodium-organomonophosphite ligand complex catalyzed hydroformylation reactions that the active catalysts be free of halogen and sulfur directly bonded to the metal, although such may not be absolutely necessary.

The organomonophosphite compounds that may serve as the ligand of the rhodium-organomonophosphite ligand complex catalyst and/or free ligand may be of the achiral (optically inactive) or chiral (optically active) type and are well known in the art. Achiral organomonophosphite ligands are preferred.

Representative organomonophosphites may include those having the formula:

<<I>>

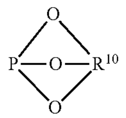

wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such organomonophosphites may be found described in greater detail, for example, in U.S. Pat. No. 4,567,306.

Representative organomonophosphites may include diorganomonophosphites such as those having the formula:

<<II>>

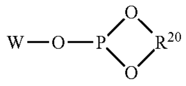

wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, bisarylene, arylene-alkylene, arylene-alkylene-arylene, arylene-oxy-arylene, arylene-$NR^{24}$-arylene wherein $R^{24}$ is as defined above, arylene-S-arylene, and arylene-S-alkylene, and the like. More preferably $R^{20}$ is a divalent aromatic radical such as disclosed more fully, for example, in U.S. Pat. Nos. 4,599,206, 4,717,775, 4,835,299, and the like.

Representative of a more preferred class of diorganomonophosphites are those of the formula:

<<III>>

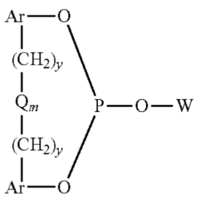

wherein W is as defined above, each Ar is the same or different and represents a substituted or unsubstituted aryl radical, each y is the same or different and is a value of 0 or 1, Q represents a divalent bridging group selected from $—C(R^{33})_2—$, —O—, —S—, $—NR^{24}—$, $Si(R^{35})_2$ and —CO—, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganomonophosphites are described in greater detail, for example, in U.S. Pat. Nos. 4,599,206, 4,717,775, and 4,835,299.

Representative organomonophosphites may include triorganomonophosphites such as those having the formula:

<<IV>>

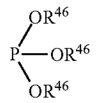

wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganomonophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)(4-biphenyl)phosphite, bis(3,6,8-tri-t-butyl-2-naphthyl)phenylphosphite, bis(3,6,8-tri-t-butyl-2-naphthyl)(4-benzoylphenyl)phosphite, bis(3,6,8-tri-t-butyl-2-naphthyl)(4-sulfonylphenyl)phosphite, and the like. A preferred triorganomonophosphite is tris(2,4-di-t-butylphenyl)phosphite. Such triorganomonophosphites are described in greater detail, for example, in U.S. Pat. Nos. 3,527,809 and 4,717,775.

As noted above, the metal-organomonophosphite ligand complex catalysts may be formed by methods known in the art. In a preferred embodiment, the metal in the metal-organomonophosphite ligand complex is rhodium. For instance, preformed rhodium hydrido-carbonyl-organomonophosphite ligand catalysts may be prepared and introduced into the reaction mixture of a hydroformylation process. More preferably, the rhodium-organomonophosphite ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with the organomonophosphite ligand for the in situ formation of the active catalyst. In some embodiments, rhodium dicarbonyl acetylacetonate is employed as a rhodium precursor and combined in the presence of a solvent with the organomonophosphite ligand to form a catalytic rhodium-organomonophosphite ligand complex precursor that is introduced into the reactor along with excess (free) organomonophosphite ligand for the in situ formation of the active catalyst. In any event, it is sufficient for the purposes of this invention that carbon monoxide, hydrogen and organomonophosphite ligand compound are all ligands that are capable of being complexed with the metal and that an active metal-organomonophosphite ligand catalyst is present in the reaction mixture under the conditions used in the hydroformylation reaction. Carbonyl and organomonophosphite ligands, if not already complexed with the initial rhodium, may be complexed to the rhodium either prior to, or in situ during the hydroformylation process.

By way of illustration, an exemplary catalyst precursor composition for use in some embodiments consists essentially of a solubilized rhodium carbonyl organomonophosphite ligand complex precursor, a solvent and, optionally, free organomonophosphite ligand. The preferred catalyst precursor composition can be prepared by forming a solution of rhodium dicarbonyl acetylacetonate, an organic solvent and a organomonophosphite ligand. The organomonophosphite ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organomonophosphite ligand complex precursor are soluble can be employed. The amounts of rhodium complex catalyst precursor, organic solvent and organomonophosphite ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organomonophosphite ligand, to form the active complex catalyst as explained above. The acetylacetone that is freed from the precursor catalyst under hydroformylation conditions is removed from the reaction medium with the product aldehyde and thus is in no way detrimental to the hydroformylation process. The use of such rhodium complex catalytic precursor compositions provides a simple economical and efficient method for handling the rhodium precursor and hydroformylation start-up.

Accordingly, the metal-organomonophosphite ligand complex catalyst (e.g., rhodium-organomonophosphite ligand complex catalyst) used in the process of this invention consists essentially of the metal complexed with carbon monoxide and a organomonophosphite ligand, said ligand being bonded (complexed) to the metal. Moreover, the terminology "consists essentially of", as used herein, does not exclude, but rather includes, hydrogen complexed with the metal, in addition to carbon monoxide and the organomonophosphite ligand. Further, such terminology does not exclude the possibility of other organic ligands and/or anions that might also be complexed with the metal. Materials in amounts that unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organomonophosphite ligand complex catalyst may be present as a result of being ligands bound to a precursor catalyst and/or as a result of in situ formation, e.g., due to the hydrogen and carbon monoxide gases employed in hydroformylation process.

As noted, the hydroformylation process of this invention involves the use of a metal-organomonophosphite ligand complex catalyst (e.g., rhodium-organomonophosphite ligand complex catalyst) as described herein. Mixtures of such catalysts can also be employed if desired. The amount of metal-organomonophosphite ligand complex catalyst present in the reaction fluid of a given hydroformylation process encompassed by this invention need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 50 ppmw to 1000 ppmw, calculated as free metal in the reaction medium, should be sufficient for most processes, while it is generally preferred to employ from 100 to 500 ppmw of metal. Analytical techniques for measuring catalytic metal concentrations are well known to the skilled person, and include atomic absorption (AA), inductively coupled plasma (ICP) and X-ray fluorescence (XRF); AA is typically preferred.

In addition to the metal-organomonophosphite ligand complex catalyst (e.g., rhodium-organomonophosphite ligand complex catalyst), free organomonophosphite ligand (i.e., ligand that is not complexed with the metal) may also be present in the reaction medium. The free organomonophosphite ligand may correspond to any of the above-defined organomonophosphite ligands discussed above as employable herein. It is preferred that the free organomonophosphite ligand be the same as the organomonophosphite ligand of the metal-organomonophosphite ligand complex catalyst employed. However, such ligands need not be the same in any given process. The hydroformylation process may involve from 0.1 moles or less to 100 moles or higher of free organomonophosphite ligand per mole of metal in the reaction medium. Preferably, the hydroformylation process is carried out in the presence of from 1 to 50 moles of free organomonophosphite ligand per mole of metal present in the reaction medium. The concentration of organomonophosphite is typically measured by high pressure liquid chromatography (HPLC) or $^{31}P$ NMR spectroscopy. Since it is more preferred to produce non-optically active aldehydes by hydroformylating achiral olefins, the more preferred organomonophosphite ligands are achiral type organomonophosphite ligands, especially those encompassed by Formula (I-IV) above. If desired, make-up or additional organomonophosphite ligand can be supplied to the reaction medium of the hydroformylation process at any time and in any suitable manner, e.g. to maintain a predetermined level of free ligand in the reaction medium.

The hydroformylation products may be asymmetric, non-asymmetric or a combination thereof, with the preferred products being non-asymmetric. The process may be conducted in any batch, continuous or semi-continuous fashion and in some embodiments, involves a catalyst liquid recycle operation.

The liquid recycle procedure generally involves withdrawing a portion of the liquid reaction fluid containing the catalyst and aldehyde product from the hydroformylation reactor, i.e., reaction zone, either continuously or intermittently, and recovering the aldehyde product therefrom by distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. Nos. 5,288,918, 8,404,903, and 10,023,516. Condensation of the volatilized materials, and separation and further recovery thereof, e.g., by further distillation, can be carried out in any conventional manner, the crude aldehyde product can be passed on for further purification and isomer separation, if desired.

Unreacted olefinic starting material may be separated from the product aldehydes by conventional means, for example, by distillation. The olefin thus recovered may then be recycled back to the reaction zone, or may be added to the reaction fluid at one or more locations between the reaction zone and the strip gas vaporizer.

The hydroformylation reaction mixture compositions employable herein can and normally will contain minor amounts of additional ingredients such as those that have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation process encompassed by this invention may include any suitable hydroformylation conditions heretofore employed for producing optically active and/or non-optically active aldehydes. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically, the carbon monoxide and hydrogen partial pressures may each independently range from 1 to 6,900 kPa, and preferably from 34 to 3,400 kPa. In general, $H_2$:CO molar ratio of gaseous hydrogen to carbon monoxide in a reaction zone may range from 1:10 to 100:1 or higher, the more preferred hydrogen to carbon monoxide molar ratio being from 1:10 to 10:1.

In general, the hydroformylation process may be conducted at any operable reaction temperature. Hydroformylation reaction temperatures of 70° C. to 120° C. are generally preferred for branched internal olefinic starting materials. It is to be understood that when non-optically active aldehyde products are desired, achiral type olefin starting materials and organomonophosphite ligands are employed and when optically active aldehyde products are desired prochiral or chiral type olefin starting materials and organomonophosphite ligands are employed. The hydroformylation reaction conditions employed will be governed by the type of aldehyde product desired.

The hydroformylation process of this invention may be carried out using one or more suitable reactors such as, for example, a fixed bed reactor, a tubular reactor, a venturi reactor, a bubble column reactor, a continuous stirred tank reactor (CSTR) or a slurry reactor. The optimum size and shape of the reactor will depend on the type of reactor used. The at least one reaction zone employed in this invention may be a single vessel, a single vessel with a plurality of zones within it such as described, for example, in U.S. Pat. No. 5,728,893, or may comprise two or more discrete vessels.

In one embodiment, the hydroformylation may be carried out in a multistaged reactor such as described, for example, in U.S. Pat. No. 5,728,893. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

The hydroformylation process utilized in this invention is conducted in a continuous fashion, with the recycle of unconsumed starting materials. The reaction can be conducted in a single reaction zone or in a plurality of reaction zones, in series or in parallel. The materials of construction employed should be substantially inert to the starting materials during the reaction and the fabrication of the equipment should be able to withstand the reaction temperatures and pressures. Means to introduce and/or adjust the quantity of starting materials or ingredients introduced continuously into the reaction zone during the course of the reaction can be conveniently utilized in the process especially to maintain the desired molar ratio of the starting materials. The starting materials and/or recycled olefin may be added to each or all the reaction zones in series.

The hydroformylation process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

A typical hydroformylation process using a metal-organomonophosphite ligand complex catalyst, for which the inventive process can be utilized, is carried out in a continuous manner and comprises: (a) feeding C7-C20 olefins (e.g., an olefin stream comprising at least a majority of C8 olefin), carbon monoxide and hydrogen to a reaction zone containing a reaction fluid, where the reaction fluid comprises a solvent, the metal-organomonophosphite ligand complex catalyst, and free organomonophosphite ligand; (b) maintaining reaction temperature and pressure conditions favorable to the hydroformylation of the olefinic starting material(s); (c) supplying make-up quantities of the mixed C7-C20 olefins (including recycled olefins), carbon monoxide, and hydrogen to the reaction zone as those reactants are consumed; (d) separating the desired product aldehyde(s) from the reaction fluid in a separation zone; (e) recovering unreacted olefins from the crude product aldehyde(s) by a distillation; and, optionally (f) adding additional rhodium and/or organomonophosphite ligand to maintain target concentrations.

General examples of liquid recycle hydroformylation processes are well known in the art and involve returning the metal-ligand complex catalyst fluid separated from the desired aldehyde reaction product(s) to one or more reaction zones, such as disclosed, for example in U.S. Pat. Nos. 4,148,830; 4,668,651; 4,774,361; 5,102,505 and 5,110,990.

Separation of the desired aldehyde product from the metal-organomonophosphite complex catalyst containing reaction fluid may take place at any suitable temperature desired. In general, it is preferred that such separation take place at relatively low temperatures, such as below 150° C., and more preferably at a temperature in the range of from 50° C. to 140° C.

Embodiments of hydroformylation processes of the present invention utilize a strip gas vaporizer in the separation zone such as is described for example in U.S. Pat. Nos. 8,404,903 and 10,023,516. In such an embodiment, the reaction fluid is introduced to a vaporizer at elevated temperature along with a stream of flowing gas comprising carbon monoxide and optionally hydrogen and nitrogen (strip gas), which becomes saturated with volatile components comprising product aldehydes and unreacted olefins. The gaseous stream exits the vaporizer and passes through a condenser (a "strip gas condenser") to generate a liquid, crude product stream comprised of product aldehydes and olefins, and a gaseous stream comprised of carbon monoxide, residual product aldehydes and olefins which remained in the gaseous phase after passing through the strip gas condenser. At least a portion of the gaseous stream is recycled and incorporated into the strip gas using a compressor or blower (recycle gas). The concentration of components that may be condensed at moderate temperatures and pressures such as unreacted olefins in the strip gas is determined in part by the temperature of the strip gas condenser. For example, lowering the temperature of the strip gas condenser will result in more condensable components being removed from the gaseous stream as liquids, thereby lowering their concentration in the recycle gas. Conversely, raising the strip gas condenser temperature will result in a higher concentration of condensable components returning to the vaporizer in the recycle gas. The non-volatiziled material (referred to herein as "tails" or "vaporizer tails") is sent back to the reaction zone (or other catalyst treatment and/or conditioning processes).

A typical vaporizer comprises a vaporization section (typically a falling film evaporator, thin film evaporator, or wiped-film evaporator) and the liquid and gaseous stream enters a separation zone wherein the liquid and gases are separated. This separation zone is herein referred to as the "catchpot". The residual liquid phase (vaporizer tails) comprises non-volatiled components such as the catalyst, free ligand, high-boiling solvents and heavies and is sent back to the reaction zone. The gaseous phase proceeds to a strip gas condenser to recover desired product and the stripping gas as described above.

In one embodiment, the separation zone comprises a carbon monoxide (CO) strip gas vaporizer such as is described in U.S. Pat. No. 10,023,516; such an embodiment employs a strip gas rich in CO.

In conventional processes, the ratio of the mass of reaction fluid entering the strip gas vaporizer (feed) to the mass of the non-volatilized catalyst-containing fluid leaving the strip gas vaporizer (tails) is maintained typically within a range of greater than 1 to 3. If this feed to tails ratio is too high (e.g. ≥4) in such processes, the catalyst will become highly concentrated within the strip gas vaporizer which may exacerbate rhodium loss. Conversely, if the feed to tails ratio is too low, the rate of aldehyde removal will limit production rates.

The present invention has found that a higher feed-to-tails ratio can be used if the resulting concentrated catalyst stream (the vaporizer tails) is treated with olefin as soon as possible. For example, in some embodiments, processes of the present invention can operate the strip gas vaporizer at a feed to tails ratio of 1.5 to 4. In some embodiments, the feed to tails ratio is 1.9 to 2.5. This addition not only dilutes the stream to maintain solubility but also stabilizes the rhodium catalyst itself against undesirable degradation processes. The higher feed-to-tails ratio improves production rates and heavies removal, and thus is an advantaged process.

In some embodiments, the solubility of the catalyst and catalyst components is increased by the addition of a C7-C20 olefins stream (or mixed C8 olefins stream or mixed C9 olefins stream) to the vaporizer tails stream.

Processes of the present invention can advantageously improve rhodium accountability in continuous liquid recycle hydroformylation processes in which C7-C20 olefins such as mixed C8 olefins or mixed C9 olefins are hydroformylated in the presence of rhodium-organomonophosphite catalyst compositions. In prior reaction processes, the measured concentration of rhodium in a reaction fluid has been observed as declining over time. The concentration of rhodium can be measured using a variety of techniques including, for example, atomic absorption (AA) and inductively coupled plasma (ICP). Unless otherwise specified herein or in the claims, the amount of rhodium in a fluid is measured using atomic absorption. In using processes of the present invention, the rate at which the concentration of rhodium declines in a reaction is slower using the inventive process than observed in typical processes for the hydroformylation of mixed C8 olefins or mixed C9 olefins using rhodium and an organomonophosphite ligand.

In one embodiment of the present invention, a process to improve rhodium accountability in a continuous liquid recycle hydroformylation process comprises contacting in a reaction zone reactants comprising C7-C20 olefins, hydrogen, and carbon monoxide in the presence of a catalyst comprising rhodium and an organomonophosphite ligand to form a reaction fluid, wherein the feed rate of olefins to the reaction zone is greater than 100 kilograms/hour; providing the reaction fluid to a strip gas vaporizer to produce a product stream and a vaporizer tails stream; measuring the C7-C20 olefin content in the vaporizer tails stream; and adding a C7-C20 olefins stream comprising at least 50 weight percent C7-C20 olefins to the vaporizer tails stream to maintain the C7-C20 content in vaporizer tails stream above 2 percent by weight. In some embodiments, the C7-C20 olefin stream that is added to the vaporizer tails stream comprises at least 70 weight percent C7-C20 olefins, or at least 70 weight percent C7-C20 olefins, or at least 80 weight percent C7-C20 olefins, or at least 85 weight percent C7-C20 olefins, or at least 90 weight percent C7-C20 olefins, or at least 95 weight percent C7-C20 olefins. In some embodiments, the vaporizer tails stream, following addition of the C7-C20 olefins stream, comprises up to 20 percent by weight C7-C20 olefins in some embodiments. In some embodiments, the vaporizer tails stream, following addition of the mixed C7-C20 olefins stream, comprises 2.5 to 15 percent by weight C7-C20 olefins, or 3 to 10 percent by weight C7-C20 olefins. In some embodiments, a majority of the C7-C20 olefins contacted in the reaction zone are C8 olefins.

In some embodiments, the C7-C20 olefin stream that is added to the vaporizer tails stream is a stream of fresh C7-C20 olefins (i.e., not previously present in the process). In some embodiments, a majority of the C7-C20 olefins in the C7-C20 olefins stream added to the vaporizer tails stream are fresh olefins. In some embodiments, the C7-C20 olefin stream that is added to the vaporizer tails stream comprises olefins that are removed from the product stream. In some embodiments, a majority of the C7-C20 olefins in the C7-C20 olefins stream added to the vaporizer tails stream are olefins that are removed from the product stream. In some embodiments, at least 95 weight percent, or in some embodiments at least 99 weight percent, of the C7-C20 olefins in the C7-C20 olefins stream added to the vaporizer tails stream are olefins that are removed from the product stream.

In another embodiment of the present invention, a process to improve rhodium accountability in a continuous liquid recycle hydroformylation process comprises contacting in a reaction zone reactants comprising mixed C8 olefins, hydrogen, and carbon monoxide in the presence of a catalyst comprising rhodium and an organomonophosphite ligand to form a reaction fluid, wherein the feed rate of olefins to the reaction zone is greater than 100 kilograms/hour; providing the reaction fluid to a strip gas vaporizer to produce a product stream and a vaporizer tails stream; measuring the C8 olefin content in the vaporizer tails stream; and adding a mixed C8 olefins stream comprising at least 50 weight percent C8 olefins to the vaporizer tails stream to maintain the C8 content in vaporizer tails stream above 2 percent by weight. In some embodiments, the mixed C8 olefins stream that is added to the vaporizer tails stream comprises at least 70 weight percent C8 olefins, or at least 70 weight percent C8 olefins, or at least 80 weight percent C8 olefins, or at least 85 weight percent C8 olefins, or at least 90 weight percent C8 olefins, or at least 95 weight percent C8 olefins. In some embodiments, the vaporizer tails stream, following addition of the mixed C8 olefins stream, comprises up to 20 percent by weight C8 olefins in some embodiments. In some embodiments, the vaporizer tails stream, following addition of the mixed C8 olefins stream, comprises 2.5 to 15 percent by weight C8 olefins, or 3 to 10 percent by weight C8 olefins.

In some embodiments, the mixed C8 olefins stream that is added to the vaporizer tails stream is a stream of fresh C8 olefins (i.e., not previously present in the process). In some embodiments, a majority of the C8 olefins in the mixed C8 olefins stream added to the vaporizer tails stream are fresh olefins. In some embodiments, the mixed C8 olefins stream that is added to the vaporizer tails stream comprises olefins that are removed from the product stream. In some embodiments, a majority of the C8 olefins in the mixed C8 olefins stream added to the vaporizer tails stream are olefins that are removed from the product stream. In some embodiments, at least 95 weight percent, or in some embodiments at least 99 weight percent, of the C8 olefins in the mixed C8 olefins stream added to the vaporizer tails stream are olefins that are removed from the product stream.

In another embodiment of the present invention, a process to improve rhodium accountability in a continuous liquid recycle hydroformylation process comprises contacting in a reaction zone reactants comprising mixed C9 olefins, hydrogen, and carbon monoxide in the presence of a catalyst comprising rhodium and an organomonophosphite ligand to form a reaction fluid, wherein the feed rate of olefins to the reaction zone is greater than 100 kilograms/hour; providing the reaction fluid to a strip gas vaporizer to produce a product stream and a vaporizer tails stream; measuring the C9 olefin content in the vaporizer tails stream; and adding a mixed C9 olefins stream comprising at least 50 weight percent C9 olefins to the vaporizer tails stream to maintain the C9 content in vaporizer tails stream above 2 percent by weight. In some embodiments, the mixed C9 olefins stream that is added to vaporizer tails stream comprises at least 70 weight percent C9 olefins, or at least 70 weight percent C9 olefins, or at least 80 weight percent C9 olefins, or at least 85 weight percent C9 olefins, or at least 90 weight percent C9 olefins, or at least 95 weight percent C9 olefins. In some embodiments, the vaporizer tails stream, following addition of the mixed C9 olefins stream, comprises up to 20 percent by weight C9 olefins in some embodiments. In some embodiments, the vaporizer tails stream, following addition of the mixed C9 olefins stream, comprises 2.5 to 15 percent by weight C9 olefins, or 3 to 10 percent by weight C9 olefins.

In some embodiments, the mixed C9 olefins stream that is added to the vaporizer tails stream is a stream of fresh C9 olefins (i.e., not previously present in the process). In some embodiments, a majority of the C9 olefins in the mixed C9 olefins stream added to the vaporizer tails stream are fresh olefins. In some embodiments, the mixed C9 olefins stream that is added to the vaporizer tails stream comprises olefins that are removed from the product stream. In some embodiments, a majority of the C9 olefins in the mixed C9 olefins stream added to the vaporizer tails stream are olefins that are removed from the product stream. In some embodiments, at least 95 weight percent, or in some embodiments at least 99 weight percent, of the C9 olefins in the mixed C9 olefins stream added to the vaporizer tails stream are olefins that are removed from the product stream.

To maintain the C7-C20 olefin content (or C8 content, or C9 content) above 2 percent by weight in the vaporizer tails stream, the C7-C20 olefins stream (or mixed C8 olefins stream or mixed C9 olefins stream) can be added in a few ways. For example, in order to maintain the concentration of C7-20 olefins (or C8 olefins or C9 olefins) in the vaporizer tails stream above 2 percent by weight, additions of C7+ olefin can be made to one of several preferred places such as (1) the vaporizer catchpot bottom liquid layer or (2) at the vaporizer tails cooler or (3) immediately in front of (before) the vaporizer bottoms pump, or (4) immediately after the vaporizer bottoms pump or a combination of these locations. In other words, the stream of C7-C20 olefins (or mixed C8 olefins or mixed C9 olefins) are added to the vaporizer tails stream by one or more of the following: (a) adding the C7-C20 olefins stream (or mixed C8 olefins stream or mixed C9 olefins stream) to the the vaporizer catchpot bottom liquid layer; or (b) adding C7-C20 olefins stream (or mixed C8 olefins stream or mixed C9 olefins stream) to the vaporizer tail cooler; or (c) adding C7-C20 olefins stream (or mixed C8 olefins stream or mixed C9 olefins stream) immediately before the vaporizer bottoms pump; or (d) adding C7-C20 olefins stream (or mixed C8 olefins stream or mixed C9 olefins stream) immediately after the vaporizer bottoms pump. The concentration of C7-C20 olefins (or mixed C8 olefins or mixed C9 olefins) in the vaporizer tails stream may be determined by gas chromatography (GC) using the method such as described in the Examples section. To maintain stability, according to some embodiments, the sooner the stream of C7-C20 olefins can added to the vaporizer tails stream, the more benefit will be observed. For example, in some embodiments, if the addition is not directly into the vaporizer catch pot, the C7-C20 olefins stream should be added within 30 seconds of the fluid entering the catchpot based on the fluid flow rate.

When catchpot divider plates are used such as described in US Patent Publication No. 2017/0253549, the plates help retain the added C7-C20 olefins within the lower portion of the catchpot minimizing any olefin vaporization particularly if the olefins are added at or below the temperature of the cooling means within the catchpot (e.g., stab-in coolers). The C7-C20 olefins should be liquids at the cooled vaporizer tails temperatures and pressures to minimize flashing.

In some embodiments, the concentration of C7-C20 olefins in the vaporizer tails may be increased by adding mixed C7-C20 olefins or recycled olefins to the reaction fluid between the vaporizer catch pot and the reaction zone. A combination of mixed C7-C20 and recycled olefin may be used in some embodiments.

The amount of the C7-C20 olefin added is at least that needed to achieve at least 2 weight percent C7-C20 olefin in the vaporizer tails stream. Higher amounts of C7-C20 olefins may be employed but little advantage is expected if the concentration of C7-C20 olefins in the vaporizer tails stream is above 50 weight % C7-C20 olefin, unless needed for solubility issues. In some embodiments, the majority of the fresh C7-C20 olefin to be reacted is added directly to the reaction zone and only a portion of the fresh C7-C20 olefin is added to the vaporizer tails. This can allow for accurate control of the composition and avoid needing larger pipes. In some embodiments, all of the fresh C7-C20 olefin is fed to the reaction zone and only recycled olefin is used in the stream added to the vaporizer tails stream to maintain the C7-20 olefin content in the vaporizer tails above 2 percent by weight. In-line mixers and other means to insure good mixing are preferred prior to the stream entering the reaction zone to insure a uniform composition.

It should be understood that under the conditions present in the vaporizer tails stream (at and after the vaporizer cooler and prior to the fluid entering the reactor), the conditions are not conducive to significant hydroformylation reaction. The temperature is low, as are the syngas partial pressures. As such, little heat of reaction or olefin conversion is expected; thus, this section is not considered part of the "reaction zone" though catalyst degradation may occur in the absence of stabilizing agents such as in the present invention.

The step of contacting in a reaction zone reactants comprising C7-C20 olefins (or mixed C8 olefins or mixed C9 olefins), hydrogen, and carbon monoxide in the presence of a catalyst comprising rhodium and an organomonophosphite ligand to form a reaction fluid can be conducted as described herein. Without wishing to be bound by any particular theory, maintaining a certain concentration of C7-C20 olefins (or C8 olefins or C9 olefins) in the vaporizer tails stream from a strip gas vaporizer is believed to improve the rhodium accountability in the process (i.e., the rate at which the rhodium concentration decreases in the reaction fluid decreases). In general, the higher the molecular weight of the olefin, the more olefin is needed to obtain the same benefit.

Illustrative aldehyde products that can result from hydroformylation of C7-C20 olefins include, but are not limited to: nonanals, decanals, dodecanals, undencanal, dodecanals, tridecanals, tetradecanals, pentadecanals, hexadecanals, heptadecanals, octadecanals, nonadecanals, icosanals, henicosanals, and the like including isomers.

Illustrative aldehyde products that can result from hydroformylation of C8 olefins include, but are not limited to, isononylaldehyde, n-nonanal, 2-methyloctanal, 3-methyloctanal, 4-methyloctanal, 5-methyloctanal, 6-methyloctanal, 7-methyloctanal, 2-ethylheptanal, 2-propylhexanal, 3-propylhexanal, 4,5-dimethylheptanal, 2,3,4-trimethylhexanal, 3-ethyl-4-methylhexanal, 2-ethyl-4-methylheptanal, 2-propyl-3-methylpentanal, 2,5-dimethylheptanal, 2,3-dimethylheptanal, and the like.

Illustrative aldehyde products that can result from hydroformylation of mixed C9 olefins include, but are not limited to: n-decanal, isodecanal, 2-methylnonanal, 3-methylnonanal, 4-methylnonanal, 5-methylnonanal, 6-methylnonanal, 2-ethyloctanal, 2-propylheptanal, 3-propylheptanal, 4,5-dimethyloctanal, 2,3,4-trimethylheptanal, 2,5-dimethyloctanal, 2,3-dimethyloctanal, and the like.

Some further embodiments further comprise removing olefins from the product stream and returning a portion of the removed olefins as part of the olefins stream (e.g., C7-C20 olefins stream, mixed C8 olefins stream, mixed C9 olefins stream, etc.) to the vaporizer tails stream after the strip gas vaporizer. In some further embodiments, a majority of the olefins in the olefins stream (e.g., C7-C20 olefins stream, mixed C8 olefins stream, mixed C9 olefins stream, etc.) that is added to the vaporizer tails stream are removed olefins from the product stream.

Some embodiments of the invention will now be described in more detail in the following Examples.

EXAMPLES

All parts and percentages in the following examples are by weight unless otherwise indicated. Pressures are given as absolute pressure unless otherwise indicated.

Olefin compositions are determined by gas chromatography (GC) using the following parameters:

| |
|---|
| Column - Petrocol DH 100 m × 0.25 mm; 0.5µ film |
| Injection - 1 µL; split ratio 150:1 |
| Detector - FID at 270° C. |
| Oven program - 40° C. for 40 minutes, to 220° C. at 10° C./min; hold 5 min, to 260° C. at 5° C./min; hold 19 minutes, to 270° C.; hold 48 minutes. |

Component quantitation is based on external standard calibration; the multiple linear octene, dimethyl hexene, and methyl heptene isomers are grouped for reporting purposes.

Rhodium concentration is measured by atomic absorption spectroscopy (AA) using a Perkin Elmer PinAAcle 900F with air-acetylene flame.

Olefin A comprises 5 weight % linear octenes, 57 weight % methyl heptenes, 34 weight % dimethyl hexenes, and 4 weight % paraffins.

Olefin B comprises 25 weight % methyl heptenes and 62 weight % dimethyl hexenes with the balance comprising paraffins. The composition of Olefin B is representative of unreacted olefins which are recovered from a product stream entering a separation zone (e.g., a strip gas vaporizer) and recycled to the reaction zone.

Rhodium is added as dicarbonyl(acetylacetonato)rhodium (I).

Ligand A is tris(2,4-di-tert-butylphenyl) phosphite which has the following structure:

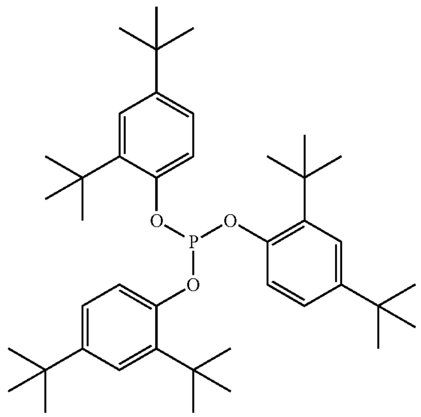

Ligand A

Examples 1-13 use an accelerated testing procedure, referred to herein as the block-in procedure to demonstrate the impact of the separation zone on the catalyst. Said testing procedure involves subjecting solubilized activated rhodium complex catalysts to high temperatures and low partial pressures of syn gas for a much longer period of time than would be experienced during a normal continuous liquid recycle hydroformylation process in order to obtain meaningful results in a practical fashion. For instance, the rhodium loss as discussed herein that may occur during a continuous liquid recycle hydroformylation process may take weeks to define quantitatively under normal aldehyde distillative recovery procedures because the catalyst is subjected to such vaporizer conditions for only a matter of minutes each day, whereas the accelerated test (block-in procedure) can be completed within hours or days by continuously maintaining the reaction product fluid at high aldehyde recovery type distillation temperatures for a prolonged period of time. Block-in segments comprise periods of time wherein the reactor is sealed under high temperatures and low syn gas partial pressures. This procedure is intended to simulate the effect of the separation zone on the catalyst solution by taking an activated rhodium catalyst solution in the absence of syngas and adding various amounts of olefin to demonstrate that the addition of olefin (such as in the vaporizer catchpot) would stabilize the catalyst against degradation.

Comparative Experiment A. A Fischer-Porter tube immersed in an oil bath at 115° C. is charged with tetraglyme (10 mL) under an atmosphere of nitrogen. Ligand A (1.7 wt %; 10 moles per mole of rhodium) and rhodium are added as stock solutions in toluene, and carbon monoxide and hydrogen are each sparged through the solution at a rate of 15 standard L/hr for about 1 hour, during which time the tube pressure is maintained at 164 psi [1.13 MPa] The gas flow is changed to nitrogen, and the solution is sparged at 10 standard L/hr while maintaining 164 psi [1.13 MPa]. After 30 minutes, the tube is sealed, and the total pressure is lowered to 115 psi [0.793 MPa]. The temperature is maintained at 115° C., and the solution is sampled periodically for rhodium analysis. This Comparative Example is intended to model the vaporizer catchpot in that the syngas is gone and the temperature is high.

Examples 1-3

The procedure of Comparative Experiment A is followed, with the exception of the addition of varying amounts of Olefin B immediately prior to reducing the pressure and sealing the tube. These Examples model the addition of an olefin stream to a vaporizer catchpot as contemplated by embodiments of the present invention.

The amount of rhodium in the solution is measured initially, after 2 days, and after 5 days. The final rhodium accountability is calculated by the following:

TABLE 1

Rhodium accountability with added C8 internal olefins.

| | Rhodium (ppmw) | | | | |
|---|---|---|---|---|---|
| | C8 internal olefins (wt %) | initial | after 2 days | after 5 days | final rhodium accountability (%) |
| Comparative Experiment A | 0 | 283 | 277 | 239 | 84 |
| Example 1 | 4.5 | 256 | 259 | 261 | 102 |
| Example 2 | 6.6 | 253 | 254 | 254 | 100 |
| Example 3 | 8.6 | 254 | 252 | 249 | 98 |
| Example 4 | 10.0 | 256 | NA | 239 | 93 |

The results of Table 1 show that the rhodium accountability is enhanced by the presence of ≥4.5 wt % C8 internal olefins.

Comparative Experiment B. The procedure of Comparative Experiment A is followed.

Examples 4-7

The procedure of Examples 1-3 is followed with the exception of Olefin B being added instead of Olefin A.

The amount of rhodium in the solution is measured initially, after 2 days, and after 5 days. Results for Comparative Experiment B and Examples 4-7 are summarized in Table 2.

TABLE 2

Rhodium accountability with added recycled C8 internal olefins.

| | total C8 internal olefins | rhodium (ppmw) | | | final rhodium accountability | final |
|---|---|---|---|---|---|---|
| | (wt %) | initial | 2 days | 5 days | (%) | appearance |
| Comparative Experiment B | 0 | 315 | 59 | 36 | 12 | dark precipitate, dark film |
| Example 4 | 2.1 | 326 | 316 | 280 | 86 | clear orange, film |
| Example 5 | 2.5 | 331 | 322 | 275 | 83 | clear orange, light film |
| Example 6 | 2.9 | 315 | 323 | 285 | 90 | clear orange, no film |
| Example 7 | 3.4 | 307 | 295 | 300 | 98 | clear yellow, no film |

The results in Table 2 indicate that the presence of greater than 2 wt % total C8 internal olefins improves rhodium accountability and that recycled olefins (e.g., olefins that might be separated from a product stream in a hydroformylation process) are effective. The appearance of the solution is an additional qualitative indication of rhodium stability; for example, a darkening of color of the formation of precipitate or film indicates that rhodium clustering is occurring.

Comparative Experiment C

A Fischer-Porter tube immersed in an oil bath at 110° C. is charged with tetraglyme (20 mL) under an atmosphere of nitrogen. Ligand A (1.7 wt %) and rhodium are added as stock solutions in toluene, and carbon monoxide and hydrogen are each sparged through the solution at a rate of 10 sL/hr for about 1 hour, during which time the tube pressure is maintained at 164 psia [1.13 MPa]. The gas flow is stopped, the tube is sealed, and the total pressure is lowered to 24 psia [0.17 MPa]. The temperature is maintained at 110° C., and the solution is sampled periodically for rhodium analysis. This Comparative Example models a vaporizer catchpot in that the syngas partial pressures are low (comparable to a strip gas vaporizer) and the temperature is high.

Example 8

The procedure of Comparative Experiment C is followed with the exception of the addition of Olefin A prior to sealing the tube (3 mL).

Example 9

The procedure of Comparative Experiment C is followed with the exception of the addition of Olefin B prior to sealing the tube (3 mL).

The results of Comparative Experiment C, Example 8 and Example 9 are summarized in Table 3.

TABLE 3

Rhodium accountability for Comparative Experiment C and Examples 8-9.

| | | | | | | Rh (ppm) | | | final |
|---|---|---|---|---|---|---|---|---|---|
| Rx | | linear octenes (wt %) | methyl heptenes (wt %) | dimethyl hexenes (wt %) | branched C8 olefins (wt %) | Initial | After 5 days | After 7 days | rhodium accountability (%) |
| 1 | Comp. Ex. C | 0 | 0 | 0 | 0 | 173 | 125 | 95 | 55 |
| 2 | Example 8 | 0.5 | 5.7 | 3.4 | 9.1 | 161 | 184 | 201 | 125 |
| 3 | Example 9 | 0 | 2.5 | 6.2 | 8.7 | 153 | 175 | 184 | 120 |

As shown in Table 3, rhodium accountability is improved by the presence of 8 to 9 wt. % branched C8 olefins.

Comparative Experiment D. A Fischer-Porter tube immersed in an oil bath at 115° C. is charged with tetraglyme (10 mL) under an atmosphere of nitrogen. Ligand A (1.7 wt %) and rhodium are added as stock solutions in toluene, and carbon monoxide and hydrogen are each sparged through the solution at a rate of 15 sL/hr for about 1 hour, during which time the tube pressure is maintained at 164 psia [1.13 MPa]. The gas flow is changed to nitrogen, and the solution is sparged at 10 sL/hr while maintaining 164 psia. After 30 minutes, the tube is sealed, and the total pressure is lowered to 115 psia [0.79 MPa]. The temperature is maintained at 115° C., and the solution is sampled periodically for rhodium analysis.

Example 10-14

The procedure of Comparative Experiment D is followed, with the exception of the addition of varying amounts of Olefin A immediately prior to reducing the pressure and sealing the tube.

The results of Comparative Experiment D and Examples 10-14 are shown in Table 4.

TABLE 4

Rhodium accountability for Comparative Experiment D and Examples 10-14.

| | linear octenes (wt %) | methyl heptenes (wt %) | dimethyl hexenes (wt %) | branched C8 olefins (wt %) | Rh (ppm) Initial | After 1 day | After 3 days | After 4 days | final rhodium accountability (%) |
|---|---|---|---|---|---|---|---|---|---|
| Comp. Ex. D | 0 | 0 | 0 | 0 | 224 | 196 | 136 | 125 | 56 |
| Example 10 | 0.2 | 2.2 | 1.3 | 3.5 | 216 | 208 | 205 | 203 | 94 |
| Example 11 | 0.3 | 3.7 | 2.2 | 5.9 | 213 | 203 | 197 | 197 | 92 |
| Example 12 | 0.4 | 4.5 | 2.7 | 7.2 | 211 | 205 | 196 | 196 | 93 |
| Example 13 | 0.5 | 5.5 | 3.3 | 8.8 | 207 | 198 | 191 | 196 | 95 |
| Example 14 | 0.6 | 6.4 | 3.8 | 10.2 | 208 | 196 | 148 | 139 | 67 |

The results of Table 4 show that the rhodium accountability improves in the presence of ≥3.5 wt % branched C8 olefins.

Examples 1-14 demonstrate that a C8 olefin concentration of >2 wt % in a vaporizer tails stream will improve rhodium accountability. These Examples also show that both internal and terminal olefins are effective.

Thus, monitoring the concentration of C7-C20 internal olefins in the vaporizer tails stream, and taking one or more actions to achieve or maintain that concentration at >2 wt %, are believed to achieve the result of some embodiments of the present invention, specifically improving the rhodium accountability in a hydroformylation process comprising rhodium, an organomonophosphite ligand and C7-C20 olefins.

Examples 15-16

For Comparative Example E, approximately 10 mL of C9 aldehyde product (derived from Olefin A), is mixed with an amount of Ligand A above the solubility limit as evidenced by the presence of solid Ligand A precipitate. For Examples 15-16, approximately 10 mL of Olefin A and 10 mL of a 1:1 by volume mixture of C9 aldehyde product:Olefin A, respectively, are each mixed with an amount of Ligand A above the solubility limit as evidenced by the presence of solid Ligand A precipitate. Each mixture is stirred thoroughly at room temperature for approximately 30 minutes, and then agitation is stopped and the solid Ligand A is allowed to settle to the bottom. The supernatant liquid is sampled and analyzed by HPLC to determine the concentration of Ligand A in solution. The results are shown in Table 5:

TABLE 5

| | Matrix | Wt % solubility of Ligand A |
|---|---|---|
| Comparative Example E | C9 Aldehyde Product | 7.3 |
| Example 15 | Olefin A | 11.6 |
| Example 16 | 1:1 Mixture | 11.0 |

The data in Table 5 show that the solubility of Ligand A is enhanced by the presence of C8 olefins (from Olefin A) compared to the product aldehyde. Ligand is often solid at the highest concentration dissolved in vaporizer tails; thus, insuring that ligand remains in solution is desired to avoid plugging of lines or damaging pumps. As demonstrated in Examples 15-16, the addition of olefin enhances ligand solubility and thus will help mitigate solubility issues.

What is claimed is:

1. A process to improve rhodium accountability in a continuous liquid recycle hydroformylation process, the process comprising:

contacting in a reaction zone reactants comprising C7-C20 olefins, hydrogen, and carbon monoxide in the presence of a catalyst comprising rhodium and an organomonophosphite ligand to form a reaction fluid, wherein the feed rate of olefins to the reaction zone is greater than 100 kilograms/hour;

providing the reaction fluid to a strip gas vaporizer to produce a product stream and a vaporizer tails stream;

measuring the C7-C20 olefin content in the vaporizer tails stream; and adding a C7-C20 olefins stream comprising at least 50 weight percent C7-C20 olefins to the vaporizer tails stream to maintain the C7-C20 content in vaporizer tails stream above 2 percent by weight.

2. The process of claim 1, wherein the stream comprising at least 50 weight percent C7-C20 olefins is added to the vaporizer tails stream by one or more of:

(a) adding the C7-C20 olefins stream to the vaporizer catchpot bottom liquid layer; or (b) adding C7-C20 olefins stream to the vaporizer tail cooler; or (c) adding C7-C20 olefins stream immediately before the vaporizer bottoms pump; or (d) adding C7-C20 olefins stream immediately after the vaporizer bottoms pump.

3. The process of claim 1, further comprising removing olefins from the product stream and returning a portion of the removed olefins as part of the C7-C20 olefins stream added to the vaporizer tails stream.

4. The process of claim 3, wherein a majority of the C7-C20 olefins in the C7-C20 olefins stream added to the vaporizer tails stream are removed olefins from the product stream.

5. The process of claim 1, wherein a majority of the olefins contacted in the reaction zone are C8 olefins.

6. The process of claim 5, wherein the product stream comprises isononyl aldehyde.

7. The process of claim 1, wherein the solubility of the catalyst and catalyst components is increased by the addition of the C7-C20 olefins stream to the vaporizer tails stream.

* * * * *